United States Patent [19]

Nakayama et al.

[11] Patent Number: 4,530,791

[45] Date of Patent: Jul. 23, 1985

[54] β-LACTAM ANTIBIOTICS

[75] Inventors: Masahito Nakayama; Akio Iwasaki; Shigeru Kimura; Sohei Tanabe; Toshimi Mizoguchi; Akira Murakami; Isamu Watanabe, all of Higashi-Murayama; Masao Okuchi, Tokorozawa; Hisakatsu Ito, Kawagoe; Toshihito Mori, Higashi-Murayama, all of Japan

[73] Assignee: Kowa Co., Ltd., Nagoya, Japan

[21] Appl. No.: 137,259

[22] Filed: Apr. 4, 1980

[30] Foreign Application Priority Data

Apr. 16, 1979 [JP] Japan .................................. 54-46516
Sep. 17, 1979 [JP] Japan ................................ 54-119139

[51] Int. Cl.³ .................... C07D 487/04; A61K 31/40
[52] U.S. Cl. .............................................. 260/245.2 T
[58] Field of Search ................. 260/245.2 T, 245.2 R; 424/270, 271

[56] References Cited

U.S. PATENT DOCUMENTS

| | | | |
|---|---|---|---|
| 4,172,129 | 10/1979 | Cole et al. | 260/245.2 T |
| 4,210,662 | 7/1980 | Eglington et al. | 260/245.2 T |
| 4,211,707 | 7/1980 | Ratcliffe | 260/245.2 T |
| 4,223,038 | 9/1980 | Smale | 260/245.2 T |
| 4,232,036 | 11/1980 | Christensen et al. | 260/245.2 T |
| 4,235,882 | 11/1980 | Cole et al. | 260/245.2 T |

FOREIGN PATENT DOCUMENTS

| | | | |
|---|---|---|---|
| 1467413 | 3/1977 | United Kingdom | 260/245.2 T |
| 1483142 | 8/1977 | United Kingdom | 260/245.2 T |
| 1489235 | 10/1977 | United Kingdom | 260/245.2 T |
| 1531141 | 11/1978 | United Kingdom | 260/245.2 T |
| 2042532 | 9/1980 | United Kingdom | 260/245.2 T |

OTHER PUBLICATIONS

Hood et al.; Jour. of Antibiotics; vol. XXXII, No. 4; pp. 295-303 (1979).

Primary Examiner—Nicholas S. Rizzo
Attorney, Agent, or Firm—Oblon, Fisher, Spivak, McClelland & Maier

[57] ABSTRACT

A novel antibiotic designated as KA-6643 and having the formula,

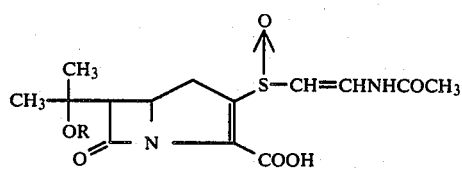

wherein R is hydrogen or —SO₃H.

3 Claims, 9 Drawing Figures

β-LACTAM ANTIBIOTICS

BACKGROUND OF THE INVENTION

1. Field of the Invention

This invention relates to a novel antibiotic and a process for producing same.

2. Description of the Invention

The present inventors have isolated various strains from soil microorganisms to investigate their producibility of antibiotics. In the studies leading to the invention, they have found that a newly isolated strain KC-6643 is capable of producing two varieties of a novel antibiotic having excellent antibacterial activities against gram-positive and gram-negative bacteria, and have succeeded in isolating such antibiotic from the culture broth, thus accomplishing the invention.

These two varieties of the antibiotic according to the invention are closely related in structure to each other. As is apparent from their physico-chemical properties and biological properties which will be described hereinafter, the antibiotic is a novel substance different from any known antibiotics.

SUMMARY OF THE INVENTION

The present invention is concerned with an antibiotic which is produced by strains belonging to Streptomyces, the antibiotic being represented by the formula (I), wherein R represents a hydrogen atom or —SO$_3$H.

In this specification, the mixture of the above-mentioned two varieties of the novel antibiotic is designated as the substance KA-6643. One of these varieties (R in the formula (I) is a hydrogen atom) is further designated as the substance KA-6643-A and the other (R in the formula (I) is —SO$_3$H) as the substance KA-6643-B.

BRIEF DESCRIPTION OF THE DRAWINGS

Other objects, features and advantages of the invention will be readily clear from the following description of certain preferred embodiments thereof, taken in conjunction with the accompanying drawings, although variations and modifications may be effected without departing from the spirit and scope of the novel concepts of the disclosure, and in which.

DETAILED DESCRIPTION OF THE PREFERRED EMBODIMENTS

The substance KA-6643 producing organism of the invention has the following taxonomic properties. It should be noted that the morphological feature in various ISP media is observed when cultured at 27° C. for 21 days by the usual methods and that the color is expressed for the mature culture in accordance with the classification of the Color Harmony Manual (Container Corporation of America), unless otherwise indicated.

I. Morphological Properties

The strain KA-6643 allows for the formation of an aerial mycelium in various media which is singly branched. The sporophore is produced on the aerial mycelium whereby the straight spore chains are provided. Each spore has a size of 0.4 to 0.5μ×0.9 to 1.0μ of a an oval to cylindrical shape and forms a chain of 20 or more spores, the surface of the spore is smooth. The spore chains are often fused together to form a sclerotium-like structure, and the fragmentation of the substrate mycelium is observed in some media used in the taxonomic studies.

II. Culture Characteristics in Various Media (1) Sucrose-nitrate agar
 Growth: Good, spreading flatly, colorless—buff (2fb)
 Aerial mycelium: Moderate, powdery, white (a)
 Soluble pigment: None (2) Glucose-asparagine agar
 Growth: Moderate, flat and buttery, cream (1½ca)—pastel yellow (2hb)
 Aerial mycelium: None
 Soluble pigment: None (3) Glycerine-Asparagine agar
 Growth: Good, warty, rugose, buff (2fg)—bamboo (2gc)
 Aerial mycelium: Good, powdery, pearl (3ba)
 Soluble pigment: None (4) Starch-inorganic salt agar
 Growth: Good, rugose, buttery, bamboo (2gc)—honey gold (2ic)
 Aerial mycelium: Good, powdery, white (a)—pearl (3ba)
 Soluble pigment: None (5) Tyrosine-agar
 Growth: Good, appreciably warty, rugose, gelatinus cinnamon (3le)
 Aerial mycelium: Good, powdery, pearl (3ba)
 Soluble pigment: None (6) Nutrient agar
 Growth: Medium, slightly warty, rugose, gelatinus colorless—light yellow (1½ea)
 Aerial mycelium: None
 Soluble pigment: None (7) Yeast extract-malt extract agar
 Growth: Abundant, rugose, buttery—gelatinus mustard (2le)
 Aerial mycelium: Good, powdery, white (a)—pearl (3ba)
 Soluble pigment: None (8) Oat meal-agar
 Growth: Moderate, flatly spreading, cream (1½ca)—butter yellow (1½ga)
 Aerial mycelium: Moderate, powdery, white (a)

Soluble pigment: None
(9) Peptone.yeast iron agar
 Growth: Good, appreciably warty, rugose, buttery, light yellow (1½ea)
 Aerial mycelium: None
 Soluble pigment: None
III. Physiological Properties
 (1) Growth temperature range: 3°–35° C.
 (2) Optimum growth temperature range: 27°–33° C.
 (3) Liquefaction of gelatin: Positive
 (4) Hydrolysis of starch: Positive
 (5) Coagulation of skim milk: Negative Peptonization of skim milk: Positive
 (6) Formation of melanoid pigment: Negative
IV. Utilization of Carbon Sources
 The utilization of carbon sources in the Pridham and Gottlieb agar medium was investigated with the following results:
 Utilized carbon sources: L-arabinose, D-xylose, D-glucose, D-furactose, inositol and L-rhamnose
 Non-utilized carbon sources: sucrose, raffinose and D-mannitol
V. The present strain contains LL-diaminopimelic acid in cell walls.

In view of the foregoing properties, the strain KC-6643 is believed to belong to the genus Streptomyces but shows characteristic properties such as fragmentation of the substrate mycelium, fusion of the spore chains and the like which are slightly different from those of the typical mycelia of the genus Streptomyces.

However, it is widely known that the strains classified as belonging to the genus Streptomyces often assume such specific structures as for example of fragmentation of hypha in the medium and abnormality in the spore chains, and hence, it is considered proper to classify the strain KC-6643 as belonging to the genus Streptomyces.

When strains of the nature where the spore chain is straight, the surface of spore is smooth, the aerial mycelium is white in color, the back side of colony does not show any characteristic tinge, and they do not produce any soluble pigment or melanoid pigment are searched out of any known strains indicated in "Bergy's Manual of Determinative Bacteriology", 8th Edition, ISP of Shirling and Gottlieb, and "The Actinomycetes" by S. A. Waksman, 2 (1961), there may be mentioned seven possible strains including *Streptomyces albovinaceus* (ISP 5136), *Streptomyces aureocircuratus* (ISP 5386), *Streptomyces baarnensis* (ISP 5232), *Streptomyces chrysomallus* (ISP 5128), *Streptomyces candidas* (ISP 5141), *Streptomyces gougeroti* (ISP 5324) and *Streptomyces griseoloalbus* (ISP 5468).

The *Streptomyces albovinaceous* (ISP 5136) is different from the strain KC-6643 in that it is poor in growth in a sucrose-nitrate agar medium and in growth at 5° C. in various media, and in liquefactivity of gelatin and further in ability to utilize carbon sources (i.e., it utilizes D-mannitol not inositol). The *Streptomyces aureocirculatus* (ISP 5386) differs from the strain KC-6643 in that it is poor in forming its aerial mycelium and grows at 37° C. but poorly at 5° C. and that it is weak in hydrolysis of starch and shows different degrees of ability to utilize carbon sources (i.e., it utilizes D-mannitol not L-rhamnose). The *Streptomyces candidas* (ISP 5141) differs from the strain KC-6643 in that it is poor in growth in a sucrose nitrate agar medium and hardly grows at 5° C., and also in the utilization of Carbon sources (i.e., it utilizes D-mannitol not inositol). The *Streptomyces gougeroti* (ISP 5324) differs from the strain KC-6643 in that it is poor in growth in a sucrose-nitrate agar medium and in forming its aerial mycelium, and in liquefactivity of gelatin, peptonization of skim milk and utilization of carbon sources (i.e., it utilizes D-mannitol not inositol nor L-rhamnose). The *Streptomyces griseoloalbus* (ISP 5468) differs from the strain KC-6643 in that it grows at 37° C. but does not grow at 5° C., and also in liquefactivity of gelatin, utilization of carbon sources (i.e., it utilizes D-mannitol) and slight yellowish tinge of aerial mycelium. The *Streptomyces baarnensis* (ISP 5232) is relatively similar in nature of culture to the strain KC-6643 but is different in that it is poor in growth at 5° C. and produces a brown soluble pigment in a gelatin medium, and is also poor in ability to utilize carbon sources (i.e., it utilizes D-mannitol not inositol). The *Streptomyces chrysomallus* (ISP 5128) is very similar in cultural characteristics to the strain KC-6643 but does not grow at 5° C. or in a skim milk medium. Further, it differs from the strain KC-6643 in the production of a yellow soluble pigment in several media and ability to utilize carbon sources (i.e., it utilizes D-mannitol not inositol).

As a strain capable of producing a product similar to a metabolite of the strain KC-6643, there are known 32 strains belonging to 11 species including *Streptomyces cattleya, Streptomyces flavogriseus, Streptomyces olivaseus, Streptomyces flavovirence, Streptomyces flaves, Streptomyces flavoviridis, Streptomyces algenteolus, Streptomyces shioyaensis, Streptomyces lipmanii, Streptomyces cremeus* and *Streptomyces gedanensis*. However, none of these known strains have such nature that the aerial mycelium is white in color and that inositol not D-mannitol is utilized.

From the above results, the present inventors have decided the strain KC-6643 to be a novel strain belonging to the genus Streptomyces and have designated as Streptomyces sp. KC-6643. This strain was deposited with the Fermentation Research Institute of the Agency of Industrial Science & Technology located at No. 1-3, Higashi 1-chome, Yatabe-machi, Tsukuba-gun, Ibaragi-ken, Japan, on Apr. 7, 1978, and has been given Acceptance No. FERM-P 4467. The strain was also deposited with the American Type Culture Collection located at No. 12301 Parklawn Drive, Rockville, Md., the United States of America, on Mar. 12, 1979, and has been given ATCC Acceptance No. ATCC 31493.

In reducing the invention to practice, not only the strain KC-6643 but also its spontaneous and artificial mutants may be used.

The culture of the present strain is feasible by any ordinary method of culturing actinomycetes. As a carbon source for media a variety of sources are usable. Preferably, starch, glycerol, maltose, dextrin, fructose, molasses and the like are used singly or in combination. Use is also made of hydrocarbons, organic acids, plant oils and the like. Nitrogen sources include soybean flour, yeast extracts, dry yeasts, peptone, meat extracts, corn steep liquors, Casamino acid, distiller's soluble, ammonium chloride, ammonium sulfate, urea, sodium nitrate and the like. These sources are used singly or in combination. If necessary, inorganic salts such as sodium chloride, potassium phosphate, sodium phosphate, magnesium sulfate, calcium chloride, calcium carbonate, calcium hydroxide, cobalt chloride, zinc sulfate, iron chloride, iron sulfate and the like, and traces of heavy metals may be added. Further, organic and inorganic substances which assist in growing the mycelia and eventually facilitate the production of the substance KA-6643 may be appropriately added. When an aerated culture method is employed, it is preferable to further add an antifoamer such as a fatty oil, silicone oil or paraffin.

Although the culture of the strain in a solid medium is possible, a liquid culture, particularly a submerged culture, is preferably used as in the case where ordinary antibiotics are produced. Such culture is conducted under aerobic conditions at temperatures ranging from 3° to 35° C., preferably 27° to 33° C.

The antibiotic KA-6643 can be produced by either a shaking culture or a tank culture. When such culture is continued for 2 to 10 days, an active substance is accumulated in the culture broth. The culture terminated at the time when the amount of the product in the culture broth reaches a maximum.

In order to isolate the substance KA-6643 from the thus obtained culture broth and purify the isolated one, various known methods may be used which are usually employed for such purposes.

For instance, the culture broth is first centrifugated or filtered to remove the mycelia therefrom, and the filtrate is subjected to any arbitrary combination of the following treatments. That is, the filtrate is passed through a basic anion exchange resin to allow the intended product to absorb the resin, and the intended product is obtained by elution with a salt solution or an aqueous methanolic solution of the salt. Examples of such ion exchange resin include strong basic, anion exchange resins such as Dowex 1×2 (The Dow Chemical Co.), Diaion PA-318, 316, 306S, 308 and 312 (Mitsubishi Chem. Ind., Ltd.), Amberlite IRA-400, 401 and 410 (Rohm & Haas Co.) and the like, and weak basic anion exchange resins such as Amberlite IRA-68. Alternatively, the culture filtrate is subjected to adsorption with an adsorbent such as active carbon, and the intended product is obtained by elution with aqueous methanol, aqueous acetone or the like.

Thereafter, the active fraction including the substance KA-6643 is passed through a strong basic anion exchange resin such for example as Dowex 1×2 to absorb the substance KA-6643 after which the substance is eluted stepwise while gradually changing a salt concentration in a phosphate buffer solution. In this elution operation, the substance KA-6643-A is eluted at an initial stage, with subsequent elution of the substance KA-6643-B, thereby separating the substance KA-6634-A and the substance KA-6643-B from each other. Alternatively, the active fraction may be passed through a column packed with a moderately polar or non-polar, hydrophobic cross-linked polymer such for example as Amberlite XAD-2 or Diaion HP-20 to separate the substance KA-6643-A and the substance KA-6643-B due to the difference in adsorptivity therebetween.

The thus obtained substance KA-6643-A and substance KA-6643-B are further subjected to gel filtration using a gel such as Biogel P-2 (BIO.RAD Lab.) or Sephadex G-10 (Pharmacia Fine Chemicals), or subjected to a reverse phase chromatography using a column packed with Bondapack $C_{18}$ (Waters Associates, Inc.), thereby obtaining highly pure substance KA-6643-A and substance KA-6643-B.

If required, both the substance KA-6643-A and the substance KA-6643-B may be converted by any usual manner to alkali metal salts, alkaline earth metal salts, primary, secondary or tertiary amine salts, or quaternary ammonium salts thereof.

The substance KA-6643 according to the invention has the following physico-chemical properties and biological properties, and exhibits antibacterial activity against gram-positive and gram-negative bacteria. Furthermore, such substance shows excellent antibacterial activity against bacteria which are resistant to various types of β-lactam antibiotics, and has β-lactamase inhibitory activity.

Figure 1:
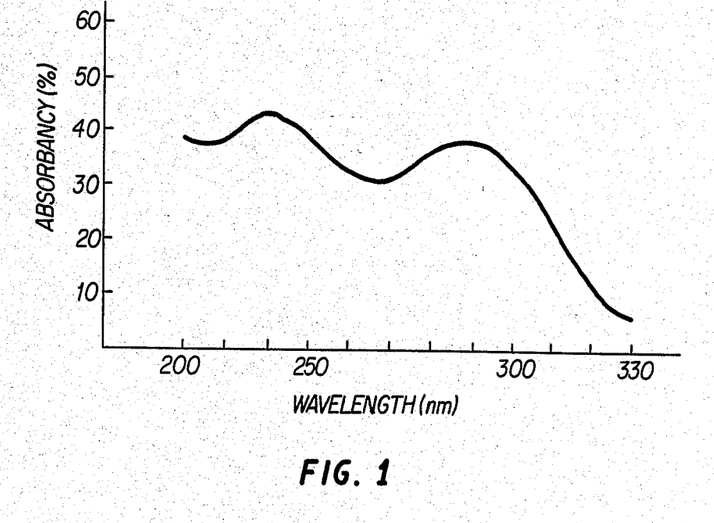
FIG. 1 is an ultraviolet absorption spectrum chart of a sodium salt of the substance KA-6643-A.
Figure 2:
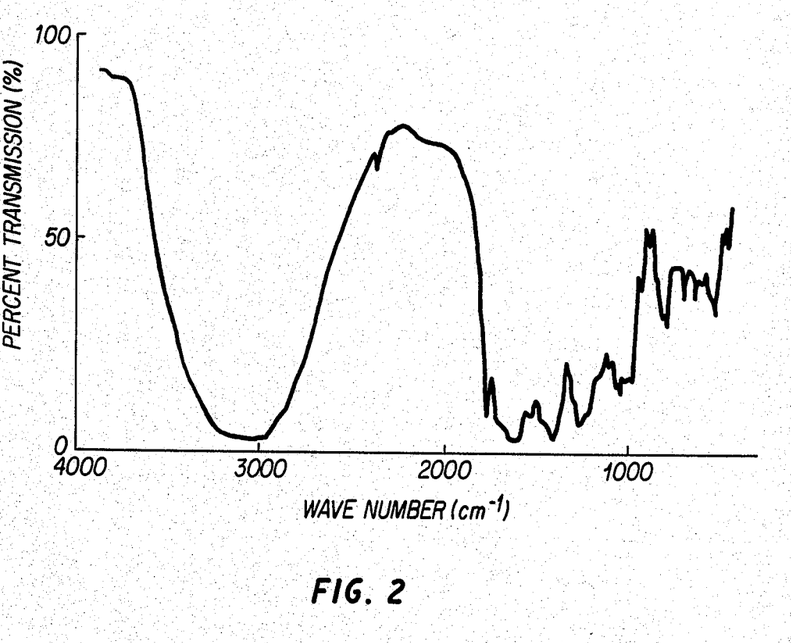
FIG. 2 is an infrared absorption spectrum chart of the sodium salt.
Figure 3:
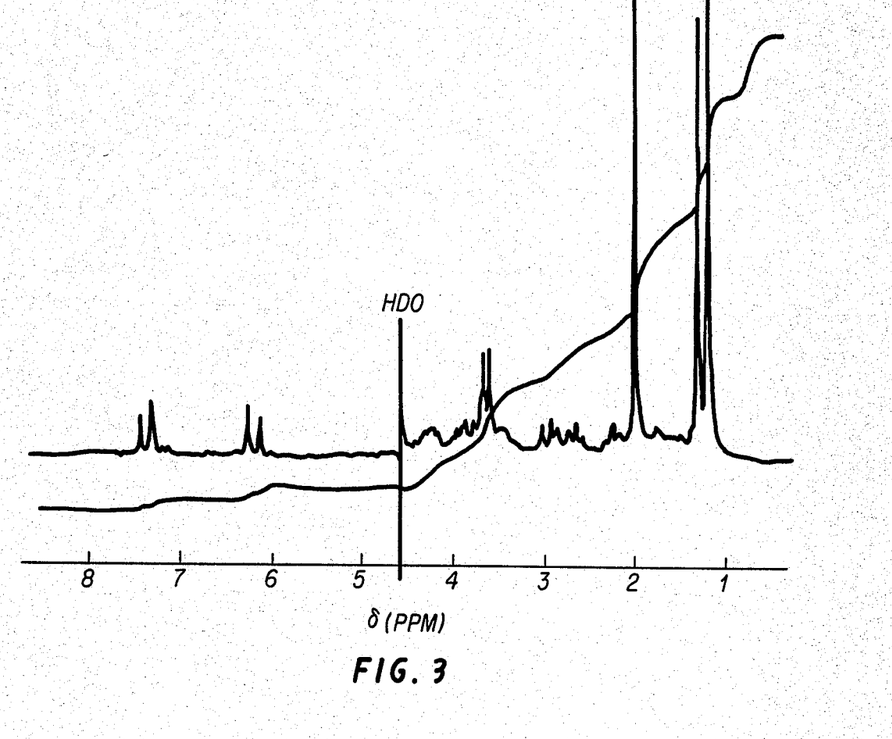
FIG. 3 is a $^1$H nuclear magnetic resonance spectrum chart of the same salt.

I. Physico-chemical Properties (A) Sodium salt of the substance KA-6643-A
(1) Appearance: White powder
(2) Melting point: Gradually decomposed above 145° C.
(3) Ultraviolet absorption spectrum: When measured in an aqueous solution, the spectrum is substantially the same as shown in FIG. 1 with maximum absorption at 240 nm and 288 nm and minimum absorption at 265 nm.
(4) Infrared absorption spectrum: When taken in KBr, the substance has substantially the same spectrum as shown in FIG. 2.
(5) Solubility in solvent: Readily soluble in water but substantially insoluble in acetone, chloroform, ethyl acetate andd petroleum ether
(6) Nuclear magnetic resonance spectrum
$^1$H Nuclear magnetic resonance spectrum: On measurement in $D_2O$, the spectrum is substantially the same as shown in FIG. 3.
(7) Thin layer chromatography
Rf value: 0.6 [plate: TLC aluminum sheet cellulose $F_{254}$, 0.2 mm (Merck & Co., Inc.); solvent: butanol-isopropyl alcohol-water (7:7:6)]
Rf value: 0.55 [plate: TLC aluminum sheet silica gel 60$F_{254}$, 0.2 mm (Merck & Co., Inc.), solvent: isopropyl alcohol-water (7:1)]
(8) High performance liquid chromatography
Elution time: 10.5 minutes
Column: μ-Bondapack $C_{18}$ (Waters Associates, Inc.), 4×300 mm
Solvent: Methanol-0.01M phosphate buffer solution (1:9), pH 6.8
Flow rate: 1 ml/min
(9) Molecular weight: 364 (Calculated from the value obtained by mass spectrometry of the monomethyl ester)
(10) Molecular formula: $C_{14}H_{17}N_2O_6SNa$ (Determined from the molecular formula of the methyl ester calculated from the results of the mass spectrometry)
(11) Stability: The half-life period at different values of pH are as follows:

| pH | KA-6643-A [t½ (hr)] | MM-4550* |
|---|---|---|
| 4.0 | 33 | 5.5 |
| 6.0 | 144 | 18 |
| 7.0 | 187 | 10.5 |
| 7.8 | 110 | 8.5 |
| 10.0 | 2.8 | 19 |

*J. Antibiot., 32, 295-304 (1979)

Solvent:
pH 4.0–7.0: McIlvaine's buffer solution (sodium phosphate-citric acid)
pH 10.0: 0.1M sodium carbonate-sodium hydrogen carbonate buffer solution
Measurement:

Ultraviolet absorption spectroscopy (B) Monomethyl ester of the substance KA-6643-A
(1) Appearance: Colorless solid
(2) Molecular weight: 356 (Mass spectrometry)
(3) Elemental analysis (as $C_{15}H_{20}N_2O_6S$)

|  | C | H | N | S |
|---|---|---|---|---|
| Calculated (%) | 50.55 | 5.66 | 7.86 | 9.00 |
| Found (%) | 50.38 | 5.45 | 7.59 | 8.60 |

Figure 4:
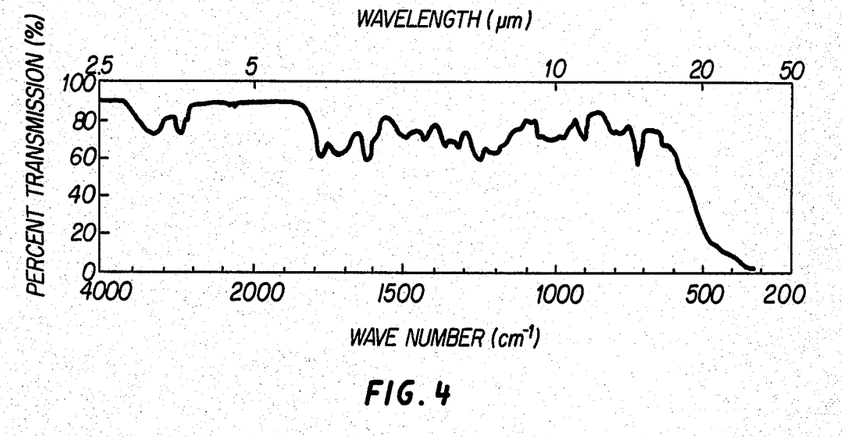
FIG. 4 is an infrared absorption spectrum chart of a methyl ester of the substance KA-6643-A.
Figure 5:
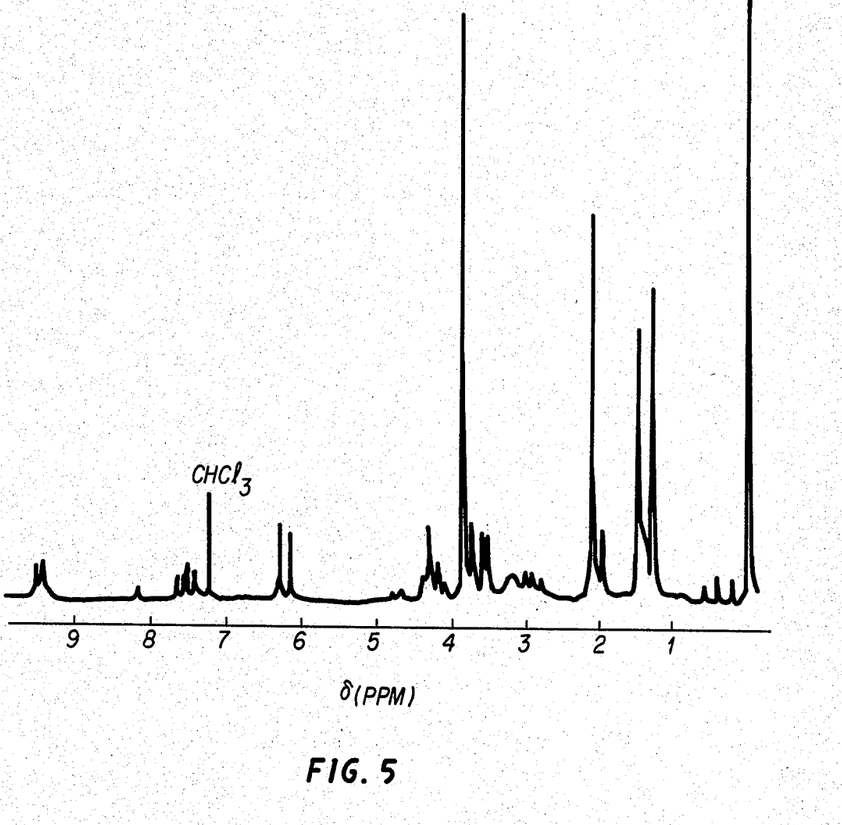
FIG. 5 is a $^1$H nuclear magnetic resonance spectrum chart of the methyl ester.
Figure 6:
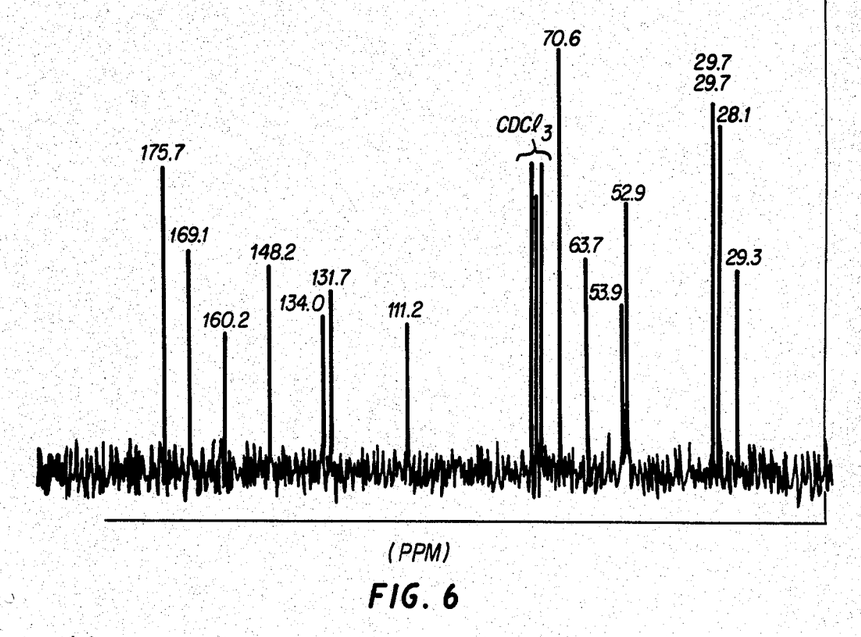
FIG. 6 is a $^{13}$C nuclear magnetic resonance spectrum chart of the same ester.

(4) Molecular formula: $C_{15}H_{20}N_2O_6S$
(5) Ultraviolet absorption spectrum: The spectrum in methanol has maximum absorption at 243 nm and 300 nm and minimum absorption at 274 nm.
(6) Infrared absorption spectrum When taken in KBr, the substance has such a substantial spectrum as shown in FIG. 4.
(7) Nuclear magnetic resonance spectrum
  (1) $^1H$ Nuclear magnetic resonance: On measurement in $CDCl_3$ using tetramethylsilane as an internal standard, the spectrum obtained is substantially the same as shown in FIG. 5.
  (2) $^{13}C$ Nuclear magnetic resonance spectrum On measurement in $CDCl_3$ using tetramethylsilane as an internal standard, the spectrum obtained is substantially the same as shown in FIG. 6.
(8) Thin layer chromatography
  Rf value: 0.44 [plate: TLC aluminum sheet silica gel 60 $F_{254}$, 0.2 mm (Merck & Co., Inc.), solvent: methylene chloride-methanol (9:11)]
(9) Specific rotation: $[\alpha]_D^{23} -96.0°$ (cl, $CH_2Cl_2$)

(C) Disodium salt of the substance KA-6643-B
(1) Appearance: White powder
(2) Melting point: Not indicated any definite point and turned yellow to brown gradually over about 130° C.
(3) Elemental analysis

| C | H | N | S |
|---|---|---|---|
| 32.5 | 3.48 | 5.17 | 11.00 (%) |

Figure 7:
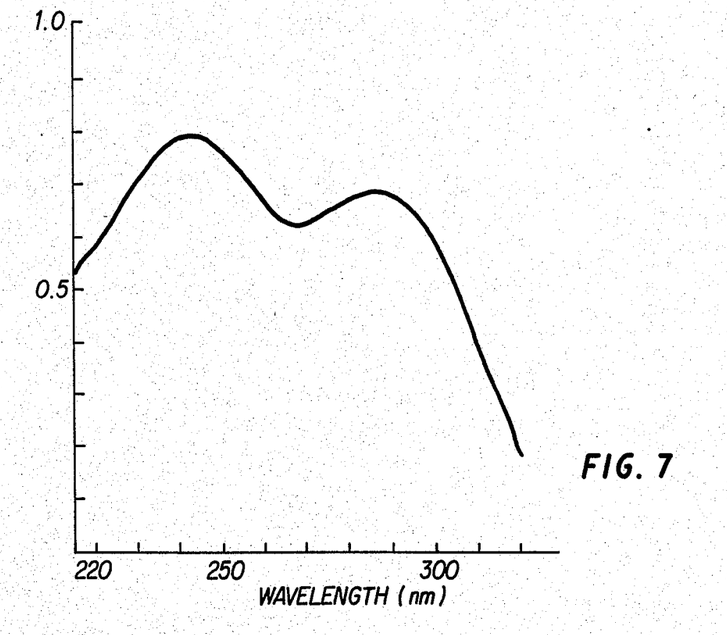
FIG. 7 is an ultraviolet absorption spectrum chart of a disodium salt of the substance KA-6643-B.
Figure 8:
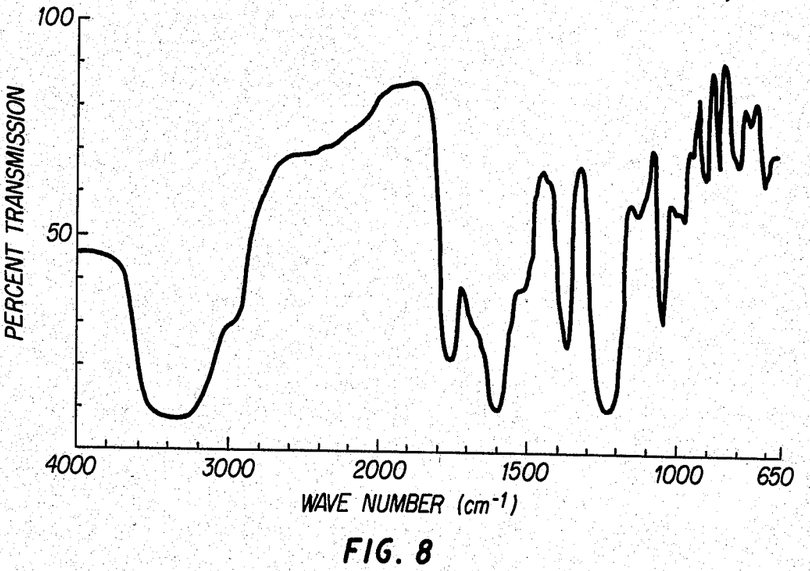
FIG. 8 is an infrared absorption spectrum chart of the disodium salt.
Figure 9:
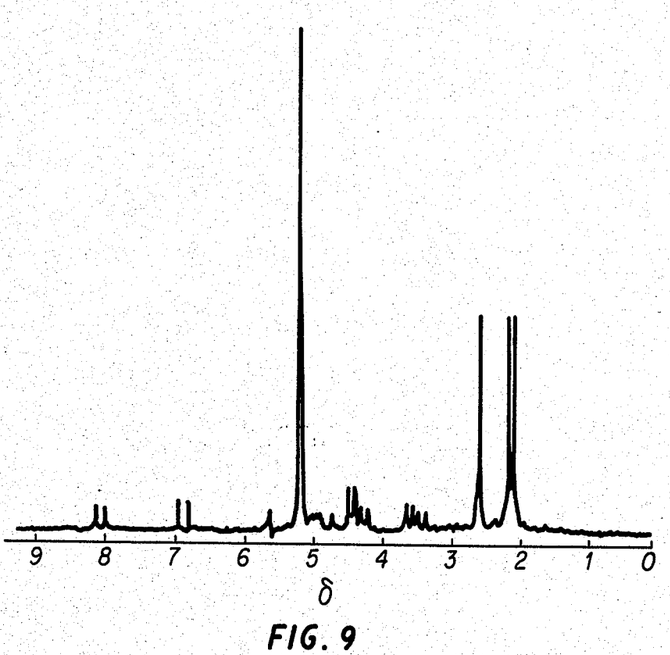
FIG. 9 is a nuclear magnetic resonance spectrum chart of the same disodium salt.

(4) Ultraviolet absorption spectrum: Substantially the same as shown in FIG. 7 and having maximum absorption bands at 240 nm and 285 nm and a minimum absorption band at 265 nm
(5) Infrared absorption spectrum: The infrared absorption spectrum of the substance taken in KBr tablets is substantially the same as shown in FIG. 8.
(6) Nuclear magnetic resonance spectrum On measurement in $D_2O$ using tetramethylsilane as an external standard, the nuclear magnetic resonance spectrum is substantially the same as shown in FIG. 9.
(7) Solubility in solvent: Readily soluble in water but substantially insoluble in organic solvents such as acetone, chloroform, ethyl acetate, petroleum ether and the like
(8) Specific rotation: $[\alpha]_D^{24} -145°$ (cl, $H_2O$)
(9) Stability: The half-life period at different values of pH are as follows:

| pH | $t_{\frac{1}{2}}$ (hr) |
|---|---|
| 4.0 | 21.8 |
| 6.0 | 210 |
| 7.0 | 170 |
| 7.8 | 130 |
| 10.0 | 7.9 |

The solvent and measurement are the same as in the substance KA-6643-A.

(10) Thin layer chromatography: The results are shown in Table 1.

TABLE 1

| Plate | Solvent | Rf value |
|---|---|---|
| TLC aluminum sheet kieserite gel 60F$_{254}$ 0.2 mm (Merck & Co., Inc.) | Butanol-ethanol-water (upper layer of 4:1:5) | 0.13 |
| TLC aluminum sheet kieserite gel 60F$_{254}$ 0.2 mm (Merck & Co., Inc.) | Isopropanol-water (7:3) | 0.85 |
| TLC aluminum sheet kieserite gel 60F$_{254}$ 0.2 mm (Merck & Co., Inc.) | Butanol-acetic acid-water (12:3:5) | 0.16 |
| TLC aluminum sheet cellulose F$_{254}$ 0.1 mm (Merck & Co., Inc.) | Butanol-isopropanol-water (7:7:6) | 0.46 |

(11) Paper chromatography
  Filter paper: Toyo fileter paper No. 51 (Toyo Filter Paper Co., Ltd.)
  Solvent: Acetonitrile-water (3:2), ascending method
  Rf value: 0.9
(12) High performance liquid chromatography
  Column: μ-Bonapack C$_{18}$ (Waters Associates, Inc.), 4×300 mm
  Solvent: 0.1M phosphate buffer solution, pH 6.8
  Flow rate: 1 ml/min
  Retention time: 23.5 minutes
(13) High voltage paper electrophoresis
  When using a high voltage paper electrophoresis device and being migrated in a 1/30M phosphate buffer solution (pH 7.0) at 3000 V for 30 minutes, the present substance moved toward the anode by 8.5 cm. Penicillin N which had been tested in a similar manner moved toward the anode by 4.4 cm.

II. Biological Properties (1) Antibacterial spectrum
  The antibacterial spectra against various microorganisms are shown in Table 2 in comparison with those of aminobenzyl penicillin (AB-Pc) and cefoxitin (CFX).

TABLE 2

| | Minimum inhibitory concentration (mcg/ml) | | | |
|---|---|---|---|---|
| Tested bacterium | KA-6643-A (Sodium salt) | KA-6643-B (Disodium salt) | AB-Pc | CFX |
| *Staphylococcus aureus* 209P JC-1 | 0.39 | 6.25 | 0.05 | 1.56 |
| *Staphylococcus epidermidis* 1228 | 0.78 | 6.25 | 0.78 | 1.56 |
| *Bacillus subtilis* 6633 | 0.2 | 6.25 | ≦0.025 | 1.56 |

TABLE 2-continued

| | Minimum inhibitory concentration (mcg/ml) | | | |
|---|---|---|---|---|
| Tested bacterium | KA-6643-A (Sodium salt) | KA-6643-B (Disodium salt) | AB-Pc | CFX |
| Escherichia coli NIHJ JC-2 | 0.05 | 1.56 | 6.25 | 6.25 |
| Klebsiella pneumoniae 602 | 0.2 | 6.25 | 12.5 | 0.78 |
| Serratia marcescens NHL | 0.2 | 6.25 | 50 | 12.5 |
| Enterobacter cloacae 977 | 0.78 | 6.25 | 100 | >100 |
| Enterobacter aerogenes 972 | 0.1 | 3.13 | 6.25 | >100 |
| Hafnia alvei 978 | 0.2 | 6.25 | 50 | 6.25 |
| Pseudomonas aeruginosa A-3 | 6.25 | 50 | >100 | >100 |
| Pseudomonas aeruginosa 10490 | 6.25 | 25 | 100 | >100 |
| Pseudomonas putida 5121 | 1.56 | 100 | >100 | >100 |
| Proteus vulgaris 874 | 0.39 | 12.5 | >100 | 6.25 |
| Proteus morganii 3168 | 0.39 | 12.5 | >100 | 6.25 |
| Proteus rettgari 13501 | 1.56 | 50 | 0.2 | 1.56 |
| Proteus inconstans Km115 | 0.78 | 12.5 | 100 | 6.25 |
| Escherichia coli EC-1 (PC ase I) | 0.2 | 3.13 | >100 | 3.13 |
| Escherichia coli EC-59 (PC ase II) | 0.05 | 1.56 | >100 | 6.25 |
| Escherichia coli EC-68 (PC ase IV) | 0.05 | 3.13 | >100 | 6.25 |
| Citrobacter 1 (PC ase) | 0.78 | 6.25 | >100 | >100 |
| Citrobacter 24 (CS ase) | 1.56 | 12.5 | >100 | >100 |
| Klebsiella 25 (PC ase) | 0.78 | 6.25 | >100 | 6.25 |
| Klebsiella 32 (CS ase) | 3.13 | 12.5 | >100 | >100 |

As is apparent from the foregoing, the substance KA-6643 exhibits intense antibacterial activity against gram-negative and gram-positive bacteria including those resistant to various penicillin- and cephalosporin-antibiotics.

(2) β-Lactamase-inhibitory activity (i) Antibacterial activity-improving action against β-lactam-resistant bacteria In the Penassay agar (12 g of which was dissolved in 500 ml of distilled water, Kyoei Pharm. Co., Ltd.) were inoculated Escherichia coli EC-1 (PC ase) and citrobacter 24 (CS ase) which were β-lactamase-producing organisms, and 10 ml of the inoculated medium was flowed on a Petri dish of 9 cm in diameter and solidified to give a test medium.

In this agar medium were placed pulp discs of 8 mm in diameter into which was introduced with 30 μg of aqueous solutions of antibiotics, respectively, followed by culturing at 37° C. for 18 hours and then measuring the diameter of an inhibiting zone around each disc. The results are shown in Table 3.

TABLE 3

| | Diameter of inhibiting zone (mm) | |
|---|---|---|
| Antibiotic composition | Medium including E. coli EC-1 | Medium including Citrobacter 24 |
| AB-Pc* (1 mg/ml) | — | — |
| KA-6643-A (10 γ/ml) | 18.0 | 16.0 |
| KA-6643-B (10 γ/ml) | — | — |
| AB-Pc (1 mg/ml) + KA-6643-A (10 γ/ml) | 20.0 | 20.0 |
| AB-Pc91 (1 mg/ml) + KA-6643-B (10 γ/ml) | 23.0 | 14.0 |

*AB-Pc: Aminobenzyl penicillin (ii) β-Lactamase-inhibitory activity

When using as β-lactamase enzyme penicillin amidohydrolase EC 3.5.2.6 (Tokyo Chem. Syn. Co., Ltd.) derived from bacteria belonging to the genus Bacillus, the $I_{50}$ value of the substance KA-6643-A was 0.5 ng/ml and that of the substance KA-6643-B was 12.8 ng/ml.

The $I_{50}$ value was measured in accordance with the method of C. Reading and M. Cole [Antimicr. Agents and Chemoth. 11, 852–857 (1977)].

Accordingly, it can be expected that the substances KA-6643-A and KA-6643-B show pronounced synergistic effects in combination with other β-lactam antibiotics.

In the light of the various properties indicated above, the present substances have been decided to be β-lactam antibiotics. While there is a known substance, i.e., MM 4550 (MC696-SY2-A), which is similar in ultraviolet absorption spectrum to the present substances, the known antibiotic is different from the substances KA-6643-A and KA-6643-B in the following respects.

(1) Paper electrophoresis

Subjected to paper electrophoresis at 3,000 V for 25 minutes

Solvent: 0.1M Phosphate buffer solution (pH 8.0)

KA-6643-A: Moved toward the anode side by 5 cm

MM 4550: Moved toward the anode side by 10.2 cm (2) High performance liquid chromatography Column: β-Bondapack $C_{18}$ (Waters Associates, Inc.) 4×30 cm Solvent: 0.05M Phosphate buffer solution (pH 7.0)

Flow rate: 1 ml/min

| Retention time: | KA-6643-A | 1 hour |
|---|---|---|
| | KA-6643 B | 30 minutes |
| | MM 4550 | 17 minutes |

From the above results, it has been found that the substance KA-6643 is a novel compound different from the known β-lactam antibiotic.

Since the substance KA-6643 according to the invention has a carboxyl group in the molecule thereof, it may be used in the form of a free acid but is preferably used in the form of salts. Suitable salts are, for example, salts of alkali or alkaline earth metals such as sodium, potassium, calcium and the like; and ammonium salts such as ammonium, trimethylamine, dimethylamine and the like. Further, the substance may be used in the form of lower alkyl esters such as methyl ester, ethyl ester and the like, or higher fatty acid esters.

A further understanding of the present invention can be obtained by reference to the following formulations and experimental results, which are provided for purposes of illustration and are not intended to be construed as limiting.

EXAMPLE 1

(i) 30 l of a liquid medium which had a composition of 3% of starch, 1.5% of soybean flour, 0.28% of potassium phosphate monobasic, 0.18% of sodium phosphate dibasic-dodecahydrate, 0.0005% of cobalt chloride.hexahydrate, 0.05% of magnesium sulfate.heptahydrate and 0.001% of ferrous sulfate and which had been adjusted to 6.0 in pH was provided, and the aliquots of 100 ml of the medium were each introduced into a 500 ml Erlenmeyer flask and sterilized. Mycelia of the strain KC-6643 were inoculated in the medium and shake-cultured at 27° C. for 4 days at 220 r.p.m.

(ii) After completion of the culture, Celite [Johns-Manville Co., Inc.] was added as a filter aid to the culture broth, and the mycelia were removed by filtration. The filtrate (25 l) was passed through a column (6×30 cm) of a strong basic anion exchange resin, Diaion PA316 (Cl⁻ type, Mitsubishi Chem. Inc., Ltd.), followed by washing with water and eluting with a 0.01M phosphate buffer solution of pH 7.0 containing 0.5M of sodium chloride to collect an active fraction. The resulting active fraction was passed through a column (4×30 cm) of active carbon and, after washing with water, was then treated with 50 V/V % aqueous acetone to collect an active fraction. The collected active fraction was passed through a column (4×40 cm) of a basic anion exchange resin, Amberlite IRA-68 (Cl⁻ type), followed by washing with water and then eluting with a 0.01M phosphate buffer solution of pH 7.0 containing 0.2M of sodium chloride to collect an active fraction. The thus collected active fraction was passed through a column (3×30 cm) of active carbon, which was washed with water and eluted with 50 V/V % aqueous acetone to collect an active fraction.

(iii) The thus obtained fraction was passed through a column (4×30 cm) of a strong basic anion exchange resin, Dowex 1×2 (100-200 mesh, Cl⁻ type), followed by washing with water and subjecting to a concentration gradient elution at a flow rate of 3 ml/min between a solution of 0.01M phosphate buffer of pH 7.0 containing 0.1M of sodium salt and a solution containing 0.4M of sodium chloride, thereby dividing the fraction into two more fractions, one being an initially eluted fraction and the other being a subsequently eluted fraction, and collecting the two fractions separately.

(iv) The initially eluted active fraction thus collected (about 1 l) was concentrated to about 100 ml under reduced pressure at below 30° C. The concentrate was passed through a column of Diaion HP-20 which had been previously washed with a 20% saline solution, followed by eluting with deionized water at a flow rate of 4 ml/min. An active fraction was collected and concentrated to about 2 ml at below 30° C., followed by freeze-drying to obtain 80 mg of a crude powder of KA-6643-A.

(v) The subsequently eluted active fraction was treated in the same manner as in step (iv), thereby obtaining 240 mg of a crude powder of KA-6643-B.

EXAMPLE 2

(i) To a medium which had a composition of 2% of starch, 1.5% of soybean flour, 0.28% of potassium phosphate monobasic, 0.18% of sodium phosphate dibasic.dodecahydrate, 0.0005% of cobalt chloride.hexahydrate, 0.05% of magnesium sulfate.heptahydrate and 0.001% of ferrous sulfate and which had been adjusted to 6.0 in pH and sterilized were inoculated mycelia of the strain KC-6643, followed by pre-culturing at 27° C. for about 48 hours to give a first seed medium. Into each of two tanks each having a volume of 200 l was charged 100 l of a medium of the same composition as used above but having 1% of cotton seed oil added. The first seed culture was inoculated to each tank in an amount of 500 ml and cultured at 30° C. by an aerated agitation system (300 rpm, a flow rate of air of 50 l/min) for 4 days.

(ii) After completion of the culture, to the culture broth (170 l) was added 10 v/v % of Dicalite Perlite 4109 (Dicalite Orient Co., Ltd.) as a filter aid, and the mycelia were removed by filtration.

The resulting filtrate (150 l) was adjusted in conductivity to 1.5 mv/cm and passed through a column (21.5×45 cm) of a strong basic anion exchange resin, Diaion PA316 (Cl⁻ type: Mitsubishi Chem. Ind., Ltd.) at a flow rate of 200 ml/min. After washing with a 0.01M phosphate buffer solution (pH 7.0), the resin was subjected to elution with a 2 v/v % methanol 0.01M phosphate buffer solution (pH 7.0) containing 2M of sodium chloride at a flow rate of 150 ml/min to collent an active fraction. The thus collected active fraction was passed through a column (16×10 cm) of Diaion HP-20, which had been adjusted with a 10 w/v % sodium chloride solution, at a flow rate of 400 ml/min and, after washing with a 10 w/v % sodium chloride solution, was eluted with deionized water at a flow rate of 200 ml/min to collect an active fraction.

(iii) The thus collected active fraction was passed through a column (6×70 cm) of a strong basic anion exchange resin, Amberlite IRA-458 (Cl⁻ type, Rohm & Haas Co.) at a flow rate of 50 ml/min and eluted with a 0.01M phosphate buffer solution (pH 7.0) containing 0.15M sodium chloride. Thereafter, the remaining active fraction was eluted with a 0.01M phosphate buffer solution (pH 7.0) containing 2M sodium chloride.

(iv) The initially eluted fraction obtained in step (iii) was subjected to the same treatment described in step (iv) of Example 1, thereby obtaining 700 mg of a crude powder of the substance KA-6643-A.

(v) The subsequently eluted active fraction was passed through a column (6×70 cm) of Diaion HP-20 which had been previously treated with a 20 w/v % aqueous sodium chloride solution and then eluted with deionized water at a flow rate of 20 ml/min to collect an active fraction. The thus collected active fraction was diluted with deionized water to have an electroconductivity of about 700 μΩ/cm and passed through a column (3×30 cm) of a weak basic anion exchange resin, DEAE-Sephadex A-25 (Pharmacia Fine Chemicals) which had been adjusted to a pH of 7.0 using a 0.01M phosphate buffer solution, followed by washing with water and eluting with a phosphate buffer solution (pH 7.0) containing 0.15M of sodium chloride at a flow rate of 35 ml/min to collect an active fraction. The thus collected eluate was concentrated under reduced pressure at below 30° C. and then passed through a column (3.5×40 cm) of Diaion HP-20 which had been previously treated with a 10 w/v % aqueous sodium chloride aqueous solution and eluted with deionized water at a flow rate of 20 ml/min to collect an active fraction. The active fraction was concentrated under reduced pressure to about 2 ml and freeze-dried to obtain 190 mg of a crude powder of the substance KA-6643-B.

The thus obtained crude powder was dissolved in 1 ml of deionized water and passed through a column (2×30 cm) of Diaion HP-20 and then eluted with deionized water at a flow rate of 1 ml/min to collect an active fraction. The thus collected active fraction was concentrated under reduced pressure and passed through a column of Sephadex G-10, followed by developing with deionized water at a flow rate of 0.2 ml/min. The active fraction was collected, concentrated under reduced pressure to about 2 ml and then freeze-dried to obtain 80 mg of a crude powder.

(vi) 80 mg of the thus obtained powder was dissolved in 0.1 ml of a 0.1M phosphate buffer solution (pH 6.8) and passed through a column (0.8×120 cm) of Bondapack $C_{18}$/Polasil B (Waters Associates, Inc.) which had been pretreated with a 0.1M phosphate buffer solution, followed by eluting with the same buffer solution at a flow rate of 6 ml/min to collect an active fraction. The active fraction was passed through a column (0.9×5 cm) of active carbon, washed with deionized water and eluted with 50 w/v % water-containing ace- tone to collect an active fraction. The active fraction was concentrated under reduced pressure to about 1 ml and freeze-dried to obtain 35 mg of a purified powder of KA-6643-B.

EXAMPLE 3

120 mg of the crude powder obtained in Example 1 (iv) or Example 2 (iv) was dissolved in 1 ml of deionized water and then passed through a column (0.8×60 cm) of Bondapack C$_{18}$/Polasil B (Waters Associates, Inc.) for high performance liquid chromatography and eluted with a 0.01M phosphate buffer solution of pH 6.8 containing 2% methanol at a flow rate of 6 ml/min to collect an active fraction.

The thus collected active fraction was concentrated to 5 ml under reduced pressure and passed through a column (2×15 cm) of Diaion HP-20, which had been washed with a saline solution, followed by eluting with deionized water at a flow rate of 1 ml/min to collect an active fraction. The fraction was concentrated to 1 ml, and then passed through a column (3×150 cm) of Sephadex G-10 and eluted with deionized water at a flow rate of 1 ml/min. Thereafter, the resulting active fraction was concentrated to 2 ml under reduced pressure and freeze-dried to obtain 4 mg of a purified product of a sodium salt of KA-6643-A.

What is claimed is:
1. An antibiotic substance represented by the formula

2. The antibiotic substance according to claim 1, wherein said antibiotic substance is in the form of a pharmaceutically acceptable salt.
3. The antibiotic substance according to claim 2, wherein said antibiotic substance is in the form of the sodium salt.

* * * * *